Figure 1:
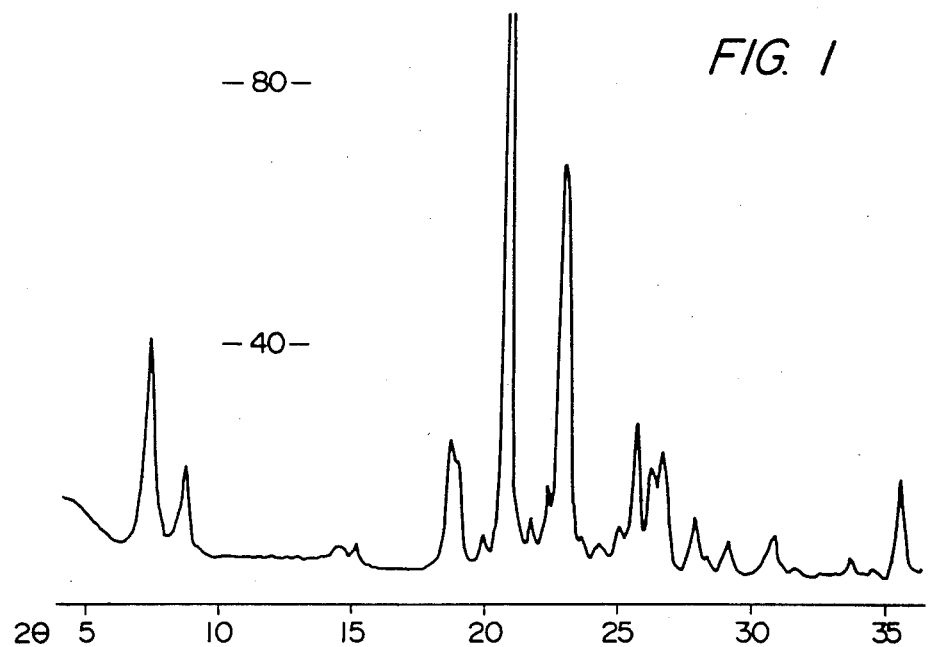

United States Patent [19]

Sumitani et al.

[11] Patent Number: 4,557,919
[45] Date of Patent: Dec. 10, 1985

[54] PRODUCTION OF CRYSTALLINE ZEOLITES

[75] Inventors: Koji Sumitani; Tokuji Sakai; Yasuo Yamasaki; Tamio Onodera, all of Matsuyama, Japan

[73] Assignee: Teijin Petrochemical Industries Ltd., Tokyo, Japan

[21] Appl. No.: 598,691

[22] Filed: Apr. 10, 1984

[30] Foreign Application Priority Data

Apr. 12, 1983 [JP] Japan .................................. 58-63052
Jul. 5, 1983 [JP] Japan ................................ 58-120952

[51] Int. Cl.$^4$ ............................................. C01B 33/28
[52] U.S. Cl. ..................................... 423/329; 423/328; 423/332; 423/335; 502/62; 502/77
[58] Field of Search ................................. 423/326–332, 423/335; 502/62, 77

[56] References Cited

U.S. PATENT DOCUMENTS 3,832,449  8/1974  Rosinski et al. ...................... 423/328
4,061,717 12/1977  Kerr et al. ............................ 423/329
4,427,787  1/1984  Miale ..................................... 502/71

FOREIGN PATENT DOCUMENTS 0042226 12/1981  European Pat. Off. ............ 423/328
2077709 12/1981  United Kingdom ................ 423/328

Primary Examiner—Edward J. Meros
Attorney, Agent, or Firm—Sherman & Shalloway

[57] ABSTRACT

A process for producing a crystalline zeolite TPZ-12, which comprises maintaining a starting mixture at a temperature of at least 80° C. for a period sufficient to produce zeolite crystals, said starting mixture consisting of (a) a substance capable of yielding silica under the reaction conditions,
(b) a water-soluble alkali metal compound,
(c) water, and
(d) a diammonium compound represented by the following general formula

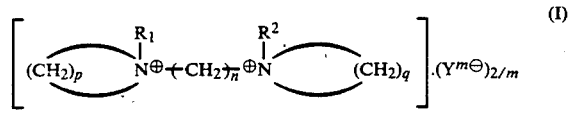

wherein $R_1$ and $R_2$ are identical or different and each represents a hydrogen atom or an alkyl group having 1 to 4 carbon atoms, p and q are identical or different and each represents an integer of 4 or 5, n is 4, 5 or 6, and y represents an anion having a valence of m, and additionally, if desired, (e) a substance capable of yielding alumina under the reaction conditions, in the particular quantities.

13 Claims, 2 Drawing Figures

PRODUCTION OF CRYSTALLINE ZEOLITES

This invention relates to a process for producing crystalline zeolites. More specifically, it pertains to a new and useful process for producing crystalline silicate zeolites and crystalline aluminosilicate zeolites, and to the use of said zeolites as catalysts for isomerization of ethylbenzene to xylene.

In the present specification, the crystalline silicate zeolites and the crystalline aluminosilicate zeolites are referred to generically as "zeolites", unless otherwise indicated.

Zeolites are characterized by having a three-dimensional network structure composed mainly of $SiO_4$ or $SiO_4$ and $AlO_4$ with a highly oriented structure of regular tetrahedron resulting from crosslinking of Si atoms or both Si and Al atoms through O. The crystalline zeolites have very many pores of a uniform size. By utilizing this property, the zeolites have been used as molecular sieves and catalysts or carriers in various syntheses.

Synthetic crystalline zeolites are in the form of very uniform and pure crystals and have excellent characteristics. For this reason, many synthetic zeolites and methods for their production have previously been proposed.

For example, "high silica" crystalline zeolites having an $SiO_2/Al_2O_3$ ratio of at least 10 are highly stable, and have high activity as catalysts for conversion of hydrocarbons, for example selective adsorption, cracking, hydrocracking, isomerization and alkylation. Many such crystalline zeolites having a high silica among which zeolites of the ZSM series comes foremost have been proposed heretofore.

Crystalline zeolites having a high silica content are produced by the action of an alkali metal cation and another cation to be used in combination upon a silica source (or both a silica and an alumina source). The structure and characteristics of the resulting crystalline zeolites differ depending upon the type of the other cation and its combination.

In the synthesis of crystalline aluminosilicate zeolites, known sources of the other cation to be used in combination with the alkali metal cation include, for example, specified quaternary ammonium compounds (for example, see U.S. Pat. Nos. 3,702,886 and 3,790,471, and DT-OS No. 2548695 and DT-OS No. 2548697), tertiary amines (see U.S. Pat. No. 3,732,188), primary amines having 2 to 10 carbon atoms (see Japanese Laid-Open Patent Publication No. 54598/1975), and alkyldiamines having 2 to 20 carbon atoms (see U.S. Pat. No. 4,139,600).

It is also known to use heterocyclic compounds in obtaining crystalline zeolites. Such a technique includes, for example, the production of mordenite by using diethylpiperidinium compounds (U.S. Pat. No. 4,366,135); the production of Nu-10 zeolite by using piperidine or morpholine (European Pat. No. 77624), the production of ZSM-39 by using pyrrolidine and a cobalt compound (U.S. Pat. No. 4,259,306); the production of ferrierite by using piperidine or an alkyl-substituted piperidine (U.S. Pat. No. 4,251,499), the production of ZSM-23 by using pyrrolidine (U.S. Pat. No. 4,076,842), the production of ZSM-35 by using pyrrolidine (U.S. Pat. No. 4,016,245), the production of zeolites similar to ZSM-5 by using a morpholine compound or an oxazolidine compound (Japanese Laid-Open Patent Publications Nos. 7816/1982 to 7818/1982), and the production of Nu-13 by using a piperazine compound (European Pat. No. 59059).

Furthermore, in the synthesis of crystalline silicate zeolites, methods have been known to use as a source of the other cation a tetraethyl ammonium ion (see U.S. Pat. Nos. 4,104,294 and 4,283,306), a tetrapropyl ammonium ion (U.S. Pat. Nos. 4,073,865 and 4,148,713) and hexamethylenediamine (see U.S. Pat. No. 4,423,021).

It is an object of this invention to provide a novel and useful process for producing crystalline zeolites which are included within a group of synthetic zeolites of the ZSM-12 series.

U.S. Pat. Nos. 3,832,449 and 3,970,544 disclose that zeolite ZSM-12 can be obtained by using a tetraethyl ammonium salt. European Pat. No. 18089 states that "it has been found that a reaction mixture containing a tetraethyl ammonium ion produces ZSM-12 only when it is crystallized after aging, and produces ZSM-5 when it is crystallized without aging". This means that the aging step can be omitted by using a methyltriethyl ammonium ion. In the working examples of this patent document, a relatively high polymer of $SiO_2$ such as colloidal silica sol or "Hi-Sil" is used as a silica source, and it does not show any example in which pure ZSM-12 zeolite was obtained from a relatively low polymer of $SiO_2$ such as sodium silicate or water glass. It will be easily presumed that ZSM-12 zeolite is more difficult to synthesize than other zeolites.

It has now been found in accordance with this invention that if a specified pyrrolidine- or piperidine-containing diammonium compound is used instead of the tetraethyl ammonium salt or methyl triethyl ammonium salt, zeolites similar in characteristic peaks of an X-ray diffraction chart to zeolite ZSM-12 (the above zeolite is referred to "TPZ-12") can be obtained stably in good yields and high purities without a prior aging treatment and irrespective of the type of the silica source.

According to the present invention, there is provided a process for producing a crystalline zeolite TPZ-12, which comprises maintaining a starting mixture at a temperature of at least 80° C. for a period sufficient to produce zeolite crystals, said starting mixture consisting of (a) a substance capable of yielding silica under the reaction conditions, (b) a water-soluble alkali metal compound, (c) water, and (d) a diammonium compound represented by the following general formula

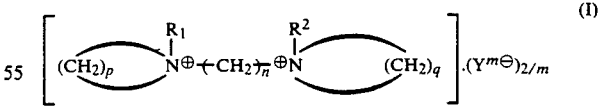

wherein $R_1$ and $R_2$ are identical or different and each represents a hydrogen atom or an alkyl group having 1 to 4 carbon atoms, p and q are identical or different and each represents an integer of 4 or 5, n is 4, 5 or 6, and y represents an anion having a valence of m, and additionally, if desired, (e) a substance capable of yielding alumina under the reaction conditions, in the quantities represented by the following expressions $15 \leqq [SiO_2]/[Al_2O_3]$ $1 \times 10^{-4} \leqq [A]/([Si]+[Al]) \leqq 1$ $1 \times 10^{-4} \leqq [OH]/([Si]+[Al]) \leqq 0.5$ $5 \leqq [H_2O]/([Si]+[Al]) \leqq 100$ $1 \times 10^{-5} \leqq [OH]/[H_2O] \leqq 1 \times 10^{-1}$ wherein

[SiO$_2$] represents the amount in moles of the substance capable of yielding silica under the reaction conditions calculated as SiO$_2$,

[Al$_2$O$_3$] represents the amount in moles of the substance capable of yielding alumina under the reaction conditions calculated as Al$_2$O$_3$,

[Si] represents the amount in moles of the substance capable of yielding silica under the reaction conditions calculated as Si,

[Al] represents the amount in moles of the substance capable of yielding alumina under the reaction conditions calculated as Al,

[A] represents the amount in moles of the diammonium compound,

[H$_2$O] represents the amount in moles of water, and

[OH] represents the total amount in moles of the alkali metal compound and the diammonium compound calculated as OH.

In the present specification and the appended claims, the quantities of the components of the starting mixture as stated above are defined as follows:

The "amount in moles of the substance capable of yielding silica under the reaction conditions calculated as SiO$_2$" denotes the amount in moles of silicon in the starting material which is calculated under the assumption that all silicon in it is converted to SiO$_2$.

The "amount in moles of the substance capable of yielding alumina under the reaction conditions calculated as Al$_2$O$_3$" denotes one-half of the amount in moles of aluminum in the starting material which is calculated under the assumption that all aluminum contained in it is converted to Al$_2$O$_3$.

The "amount in moles of the substance capable of yielding silica (or alumina) under the reaction conditions calculated as Si (or Al)" means the amount in moles of silicon (or aluminum) contained in the starting material.

The "total amount in moles of the alkali metal compound and the diammonium compound calculated as OH" denotes the amount in moles of the OH$^-$ ion obtained by subtracting the amount of an acid cation to be neutralized and the amount of the aluminum atoms contained in the resulting zeolite from the amount of the OH$^-$ ion attributed to the alkali metal compound and/or the diammonium compound added.

The present invention can give a crystalline silica zeolite or crystalline aluminosilicate zeolite called TPZ-12 stably with good reproducibility. The zeolites obtained have a very high purity.

The process of this invention will be described in greater detail below.

The "substance capable of yielding silica under the reaction conditions" used in the starting mixture in accordance with this invention (which will be referred to hereinbelow as a "silica source") may be any of those which are normally used in the production of zeolites. It may, for example, be silica powder, colloidal silica, soluble silicates, and silicic acid. Suitable silica powders are Aerosil silica, fumed silica, silica gel, and precipitated silica produced from alkali metal silicates by the precipitation method. The colloidal silica is available in various particle sizes ranging, for example, from 10 to 50 microns. Examples of the soluble silicates include water glass silicates containing 1 to 5 moles, particularly 2 to 4 moles, of SiO$_2$ and 1 mole of Na$_2$O or K$_2$O, alkali metal silicates, and silicates obtained by dissolving silica in alkali metal hydroxides. Preferred silica sources for use in the process of this invention are colloidal silica and water glass silicates.

One advantage of the process of this invention is that water glass easily available at low cost industrially can be used as the silica source. By using water glass, the desired zeolites can be obtained in the same way as in the case of using silica sol and colloidal silica.

According to the process of this invention, crystalline silicate zeolites can be obtained by heating a starting mixture containing the silica source, water, an alkali metal compound and the ammonium compound of formula (I) given hereinabove. By further adding the "substance capable of yielding alumina under the reaction conditions" (to be referred to as an "alumina source" hereinafter) to the starting mixture, crystalline aluminosilicates can be obtained.

Thus, the alumina source is not an essential starting material in the process of this invention. When it is not used, a crystalline silica zeolite is obtained. When the alumina source is used, a crystalline aluminosilicate zeolite having an alumina component can be obtained.

The alumina source which may optionally be used may be any of those which are generally employed in the production of zeolites. Examples include aluminum salts such as aluminum chloride, nitrate and sulfate; hydrated or hydratable aluminas such as colloidal alumina, pseudoboehmite, boehmite, gamma-alumina, alpha-alumina and beta-alumina trihydrate; and sodium aluminate. The aluminum salts and sodium aluminate are preferred.

The aluminosilicate mentioned above as the silica source may be used as part or the whole of the alumina source because such a compound is a common source of alumina and silica.

The alkali metal compound may preferably be in the form of a readily water-soluble salt or a hydroxide. Examples of such water-soluble alkali metal compounds include sodium hydroxide, potassium hydroxide, alkali metal aluminates such as sodium aluminate or potassium aluminate, and alkali metal silicates such as sodium silicate and potassium silicate. Sodium is an effective and desirable alkali metal in these alkali metal compounds. When the alkali metal aluminates or alkali metal silicates are used, they can serve concurrently as the alumina source and the silica source.

The diammonium compound used together with the alkali metal compounds are represented by the following general formula (I):

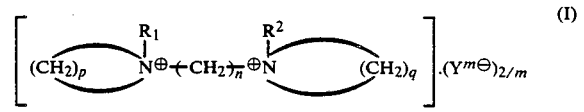

(I)

wherein R$_1$, R$_2$, p, q, n and Y are as defined hereinabove.

In the above general formula, p and q may be identical or different, but diammonium compounds of formula (I) in which p and q are identical (symmetric) are easy to synthesize. p and q represent an integer of 4 or 5. In other words, the moiety $(CH_2)_{p \text{ or } q}$ in the above formula represents a 5- or 6-membered nitrogen-containing heterocycle

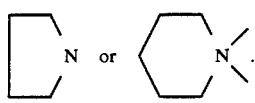

The n in the bridging member $-(CH_2)_n-$ linking the two nitrogen-containing heterocycles in the formula is a parameter which affects the crystal structure of the resulting zeolite, particularly its X-ray diffraction chart. It is important that in the present invention, n should be 4, 5 or 6. When n in formula (I) is less than 4 or larger than 6, the process of this invention does not give the desired zeolite TPZ-12 in good yields. Preferably, n is 4 or 5. When both p and q are 4, n is most preferably 5. When p and q are both 5, n is most preferably 4.

In general formula (I), $R_1$ and $R_2$ are identical or different and each represents a hydrogen atom or an alkyl group having 1 to 4 carbon atom. Desirably, both $R_1$ and $R_2$ are methyl groups.

Examples of the anion $Y^{m-}$ are $Cl^-$, $Br^-$, $I^-$, $NO_3^-$, $SO_4^{--}$, $PO_4^{---}$, and $OH^-$.

Examples of the diammonium compounds of formula (I) which can be conveniently used in the process of this invention are shown below.

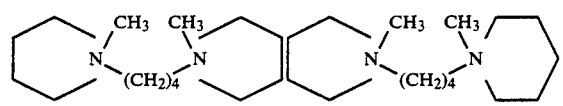

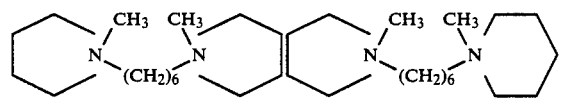

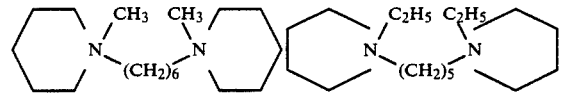

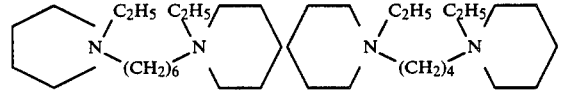

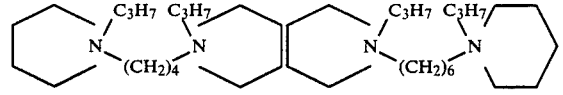

-continued

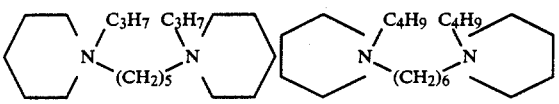

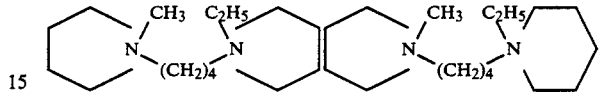

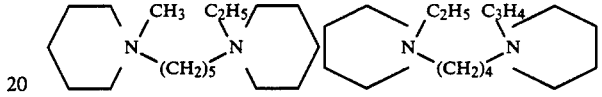

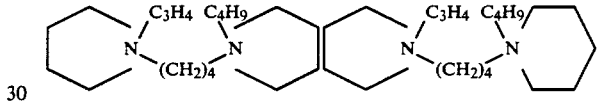

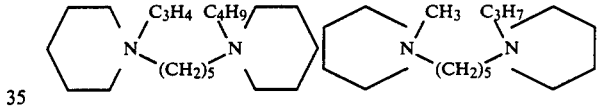

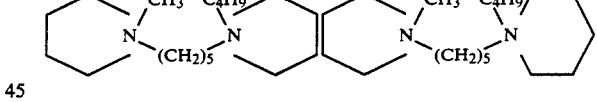

Of these, especially preferred diammonium compounds are as follows:

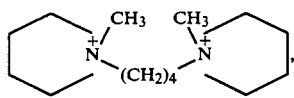

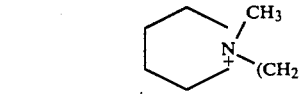

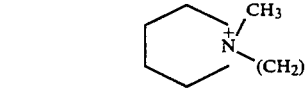

-continued

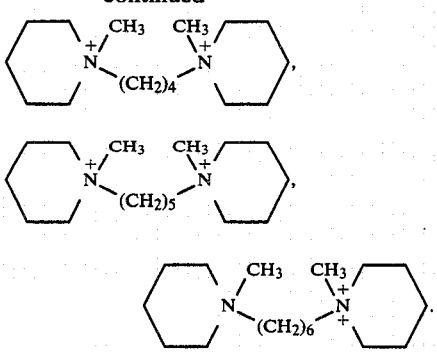

The diammonium compounds of formula (I) are either known per se, or novel. The novel compounds may be produced in the same way as in the production of the known compounds. For example, the diammonium compound can be produced by reacting a dihalide compound of the following general formula (II)

$$X_1+CH_2+_nX_2 \qquad (II)$$

wherein $X_1$ and $X_2$ are identical or different and each represents a halogen atom, and n is as defined above, with an amine compound represented by the following general formula (III-a) and/or (III-b)

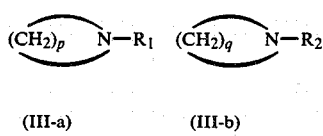

(III-a)         (III-b)

wherein $R_1$, $R_2$, p and q are as defined hereinabove.

Examples of the dihalides of formula (II) are 1,4-butane dibromide, 1,4-butane dichloride, 1,5-pentane dibromide and 1,6-hexane dibromide. Examples of preferred amine compounds of formula (III-a) or (III-b) include pyrrolidine, N-methylpyrrolidine, piperidine and N-methylpiperidine.

The dihalide of formula (II) and the amine compound of formula (III-a) and/or (III-b) may be reacted in advance and used as the diammonium compound of formula (I). Alternatively, it is possible to introduce the compounds of formula (II) and formulae (III-a) and/or (III-b) into the starting mixture for zeolite synthesis, and to form the diammonium compound of formula (I) in situ in the reaction system.

In the process of this invention, the starting mixture is prepared from the substance capable of yielding silica under the reaction conditions (silica source), the water-soluble alkali metal compound, water and the diammonium compound of formula (I) and additionally, if desired, the substance capable of yielding alumina under the reaction conditions (alumina source) in the amounts which meet the following expressions, and the desired zeolite is produced from the starting mixture.

(1) $[SiO_2]/[Al_2O_3] =$ at least 15 (when $[Al_2O_3]$ is 0, $[SiO_2]/[Al_2O_3]$ is infinity), preferably from 20 to 2,000, especially preferably from 20 to 250.

(2) $[A]/([Si]+[Al]) = 1 \times 10^{-4}$ to 1, preferably from $5 \times 10^{-4}$ to 0.5, especially preferably $1 \times 10^{-3}$ to $1 \times 10^{-1}$.

(3) $[OH]/([Si]+[Al]) = 1 \times 10^{-4}$ to 0.5, preferably $1 \times 10^{-3}$ to 0.4, especially preferably $5 \times 10^{-3}$ to 0.3.

(4) $[H_2O]/([Si]+[Al]) = 5$ to 100, preferably 10 to 50, especially preferably 15 to 50.

(5) $[OH]/[H_2O] = 1 \times 10^{-5}$ to $1 \times 10^{-1}$, preferably $1 \times 10^{-4}$ to $1 \times 10^{-1}$, especially preferably $1 \times 10^{-4}$ to $1 \times 10^{-2}$.

In the above expressions, $[SiO_2]$, $[Al_2O_3]$, $[Si]$, $[Al]$, $[A]$, $[H_2O]$ and $[OH]$ are as defined hereinabove.

It will be seen from the above conditions (3) and (5), the presence of a OH ion based on the alkali metal compound and/or the diammonium compound in the starting mixture is essential. Accordingly, when an alkali metal compound not containing a OH radical is used, the diammonium compound should be one having the above formula (I) in which a part or the whole of the anion ($Y^{m\ominus}$) is $OH^-$. Of course, so long as the conditions (3) and (5) are met, the alkali metal hydroxide and the OH-containing diammonium compound may be used together.

The alkali metal compounds, the diammonium compound, the silica source, the alumilna source are mixed in the amounts meeting the quantitative conditions (1) to (5) to form the starting mixture. By heating the mixture at a temperature and for a period of time sufficient for forming a crystalline zeolite, the zeolite TPZ-12 can be synthesized. The zeolite synthesizing reaction may be carried out by methods known per se. The preferred reaction temperature is at least 80° C., and temperatures of 100° to 200° C. are advantageous. The reaction time is usually 5 hours to 100 days, preferably 10 hours to 50 days, especially preferably 1 to 7 days. The pressure is the autogenous pressure to a higher elevated pressure. Generally, the reaction is carried out under autogenous pressure. It may be carried out in an atmosphere of an inert gas such as nitrogen gas.

The reaction of forming the crystalline zeolite is continued until the crystalline zeolite is formed by heating the reaction mixture at the desired temperature with optional stirring. After the crystals are formed, the reaction mixture is cooled to room temperature, filtered, washed with water until, for example, its ion conductivity reaches not more than 50 micromhos/cm. The crystals are then separated. If further required, the crystals can be dried. Drying may be carried out at room temperature or under atmospheric or reduced pressure. For example, it is carried out at a temperature of 50° to 130° C. for a period of about 5 to 24 hours.

The cation of the resulting crystalline zeolite is composed of an alkali metal ion and an ion based on the ammonium compound. The cation site may be replaced by an ammonium ion by, for example, causing an aqueous solution of $NH_4Cl$ to act on it.

The resulting crystals optionally replaced by an ammonium ion as mentioned above may be calcined at a temperature of generally 100° to 600° C., preferably 300° to 500° C. for a period of 8 to 24 hours, preferably 8 to 16 hours. This calcination procedure is also within the scope of this invention.

The alkali metal ion and/or the ammonium ion of the crystalline zeolite produced by the process of this invention may be replaced partly or wholly by at least one other cation. Examples of the exchangeable cation include monovalent cations such as lithium, silver and ammonium; divalent alkaline earth metal cations such as magnesium, calcium and barium; trivalent cations such as aluminum; ions of metals of Group VIII of the periodic table such as cobalt, nickel, platinum and palladium; and cations of rare earth metals. The rare earth metals include lanthanum, cerium, praseodymium, neodymium, samarium, europium, gadolinium, terbium, scandium and yttrium.

The ion exchange may be carried out by methods known per se. For example, the crystalline zeolite is treated with a water-soluble or water-insoluble medium containing the desired ion. This treatment may be achieved batchwise or continuously. The ion exchange may increase the crystallinity or activity of the crystalline zeolite in accordance with this invention.

If prior to performing the reaction of forming the crystalline zeolite as stated above, particles of the crystalline zeolite as the final desired product are caused to be present in the starting mixture, zeolites having a large particle diameter may sometimes be obtained.

Accordingly, the inclusion of the particles of the desired crystalline zeolite in the starting mixture frequently brings about favorable results.

The zeolite TPZ-12 so obtained has the composition of the following general formula (IV) in the form of an oxide in an anhydrous condition:

$$xM_{2/t}O \cdot yAl_2O_3 \cdot SiO_2 \qquad (IV)$$

wherein M represents at least one type of cation having a valence of t, x represents a number from 0 to 0.4, preferably from 0.025 to 0.08, and y is a number from 0 to 0.1, preferably from 0.005 to 0.02.

Furthermore, this zeolite TPZ-12 has at least the following significant peaks.

| Interplanar spacing d (Å) | Relative intensity (I/I$_o$) |
|---|---|
| 11.9 ± 0.5 | Moderate |
| 10.1 ± 0.5 | Weak |
| 4.74 ± 0.1 | Weak |
| 4.25 ± 0.1 | Very strong |
| 3.88 ± 0.05* | Strong |
| 3.47 ± 0.04 | Moderate to weak |
| 3.40 ± 0.04 | Weak |
| 3.34 ± 0.04 | Weak |
| 2.53 ± 0.03 | Weak |

(The asterisked peak may have a shoulder or be split.)

The relative intensity (I/I$_o$), used herein, is the intensity percentage of each peak when the intensity of the strongest peak (I$_o$) at d(Å) is taken as 100, and is defined as follows:

| Very strong | 100–60 |
|---|---|
| Strong | 60–40 |
| Moderate | 40–20 |
| Weak | 20–10 |

The above crystalline zeolite TPZ-12 is seen to have a moderate peak at d=11.9±0.5, a very strong peak at d=4.25±0.1 and a strong peak at d=3.88±0.05. As far as these peaks are concerned, this zeolite is similar to the known zeolite, ZSM-12 (see Japanese Patent Publication No. 16079/1977), but the characteristics of the other peaks are slightly different.

The zeolite TPZ-12 produced by the process of this invention is useful as a catalytic component for reforming reactions of hydrocarbons, hydrogenating isomerization reaction and hydrogenating decomposition reaction of paraffins, conversion of olefins into aromatics, isomerization reaction of olefins, conversion reactions of methanol or dimethyl ether, conversion reaction of aromatic hydrocarbons such as disproportionation reaction of toluene, methylation of toluene with methanol, disproportionation reaction of toluene and trimethylbenzene, isomerization reaction of xylenes, and isomerization reaction of ethylbenzene to xylene, and also as an adsorbent for organic compounds.

Zeolite TPZ-12 is particularly useful as an active ingredient of a catalyst for isomerization of ethylbenzene to xylene.

When the zeolite TPZ-12 in accordance with this invention is to be used as a catalyst, it is combined with other catalytically active ingredients, binders, etc. as usual.

When the zeolite TPZ-12 is used in combination with other catalyst components, it is advantageous that its proportion is generally 10 to 90% by weight, preferably 20 to 80% by weight, based on the total weight of the catalyst composition.

Advantageously, the catalyst composition may further contain a metal having both hydrogenating and dehydrogenating activities, such as platinum, palladium, nickel and rhodium. The amount of such a metal is generally 0.01 to 7% by weight, preferably 0.02 to 5% by weight, based on the weight of the catalyst composition.

Investigations of the present inventors have shown that by using a catalyst composition consisting essentially of a combination of (i) the crystalline zeolite TPZ-12 and (ii) alumina having at least platinum deposited thereon, ethylbenzene can be isomerized to xylenes in good conversions and selectivities.

Such a catalyst, in other words, comprises at least the crystalline zeolite TPZ-12, alumina and platinum, the platinum being deposited on alumina.

Roughly speaking, this catalyst composition can be obtained by the following methods (a) to (c), although other methods or partial modifications of the methods (a) to (c) may also be used.

(a) A method which comprises depositing platinum on alumina, mixing the resulting powder with a powder of the crystalline zeolite powder, and molding the mixture.

(b) A method which comprises first preparing a composition comprising alumina and the crystalline zeolite, depositing platinum on the composition, and thereafter molding the composition.

(c) A method which comprises preparing a composition comprising alumina and the crystalline zeolite, molding the composition, and depositing platinum on the molded composition.

In any of these methods, platinum can be deposited by the platinum-depositing methods usually employed in the preparation of solid catalysts. For example, alumina or a mixture of alumina and the zeolite is impregnated with an aqueous solution of a water-soluble platinum compound such as chloroplatinic acid (H$_2$PtCl$_6$), platinum chloride (PtCl$_2$) or a platinum-amine complex [for example, Pt(NH$_3$)$_4$Cl$_2$], and thereafter the water is removed by evaporation.

The catalyst composition containing alumina having platinum deposited thereon can preferably be heat-treated at a temperature of 100° to 700° C., preferably 200° to 60° C., for a period of about 1 to about 20 hours in an oxygen-containing atmosphere such as air on an atmosphere of an inert gas such as nitrogen.

Alumina used in the preparation of the aforesaid catalyst composition may be any of those materials which are generally called alumina. Preferably, it has a surface area of 50 to 400 m$^2$/g, particularly 100 to 350 m$^2$/g. There is no particular restriction on the method of producing alumina, but generally alumina obtained by heat-treating aumina hydrate at a temperature of 200° to 1,000° C. is suitable. The crystal form of alumina may be $\chi$, $\gamma$, $\eta$, $\theta$, $\delta$, $\kappa$, etc. Advantageously, alumina has an average particle diameter of 1 to 500 microns, preferably 2 to 100 microns.

The suitable weight ratio of the crystalline zeolite to alumina in the above catalyst composition is from 10:90 to 90:10, preferably from 75:25 to 25:75. If the proportion of the zeolite is smaller than the above-specified lower limit, the concentration of the zeolite in the catalyst becomes low, and to produce xylenes on an industrial scale, a reaction apparatus of a large capacity is required. This is economically disadvantageous. If the weight proportion of alumina becomes smaller than the above-specified lower limit, the activity of the catalyst to isomerize ethylbenzene to xylenes tends to be reduced undesirably.

The concentration of platinum in the catalyst composition is 0.01 to 5% by weight, preferably 0.05 to 3% by weight, based on the total weight of the zeolite and alumina. If the concentration of platinum is lower than the specified limit, the effect of including platinum, namely the activity of the catalyst to isomerize ethhylbenzene to xylenes, is reduced. On the other hand, an increase in the proportion of platinum beyond the above-specified upper limit does not correspondingly increase the action of platinum and is rather economically disadvantageous.

The catalyst composition in accordance with this invention should basically contain (i) the crystalline zeolite and (ii) alumina having at least platinum deposited thereon. Desirably, the two components are contained in an amount of at least 50%, preferably at least 70%, based on the total weight of the catalyst composition. It may contain not more than 50% by weight, preferably not more than 30% by weight, of other components. Examples of preferred other components are metals of Group VIII of the periodic table other than platinum (for example, rhodium,rhenium and iridium). There can also be used synthetic or natural refractory inorganic oxides which are generally used as binders for zeolite cataysts, such as silica, alumina, silica-alumina, kaolin and silica-magnesia.

The catalyst composition composed of the crystalline zeolite, alumina having at least platinum deposited thereon, and if required, other components may be used in reactions after it is molded into various desired forms, such as pellets or tablets.

The catalyst so prepared may be treated, prior to use, in a reducing atmosphere such as hydrogen gas at a temperature of 200° to 600° C., preferably 250° to 550° C.

The resulting catalyst composition containing the crystalline zeolite TPZ-12 is effective for production of xylenes by isomerizing ethylbenzene in the vapor phase in the presence of hydrogen. The starting ethylbenzene needs not be pure, and may, for example, be a hydrocarbon fraction containing ethylbenzene, and contains preferably at least 10 mole%, especially preferably at least 15 mole%, of ethylbenzene. The components of such a hydrocarbon fraction other than ethylbenzene are preferably such aromatic hydrocarbons as benzene, toluene, o-xylene, m-xylene, p-xylene, 1,3,5-trimethylbenzene, 1,2,4-trimethylbenzene, ethyltoluene, diethylbenzene and tetramethylbenzene. The hydrocarbon fraction may also contain a minor proportion of an alicyclic hydrocarbon such as cyclohexane, methylcyclohexane and dimethylcyclohexane.

When a hydrocarbon fraction containing ethylbenzene and various xylenes is used as a starting material in the aforesaid isomerization method, the isomerization of the xylenes into each other occurs simultaneously with the isomerization of ethylbenzene to xylenes.

The above isomerization process is carried out at a temperature of 280° to 500° C., preferably 300° to 450° C. The reaction pressure is from atmospheric pressure to 30 kg/cm$^2$, preferably from atmospheric pressure to 25 kg/cm$^2$.

In performing the above isomerization, the proportion of the starting material to be fed can be varied widely depending upon the type of the hydrocarbon material used, and/or the type of the catalyst used, etc. Advantageously, it is fed at a weight hourly space velocity (WHSV) within the range of about 0.1 to about 200, preferably about 0.1 to about 50.

In the present specification, the "weight hourly space velocity" (WHSV) is a value calculated in accordance with the following equation.

$$\frac{\text{Weight of the hydrocarbon material fed per hour}}{\text{Weight of the crystalline zeolite}}$$

The above isomerization is carried out in the presence of hydrogen. The proportion of hydrogen to be fed can be varied widely depending upon the starting material containing ethylbenzene and/or the type of the catalyst composition. The suitable proportion of hydrogen is such that the mole ratio of hydrogen to the ethylbenzene-containing material becomes generally from 1 to 30, preferably from 1 to 20.

Prior to the reaction, or when the activity of the catalyst composition has been lowered beyond a certain level as a result of the isomerization reaction, the catalyst composition may be subjected to the zeolite chlorination treatment generally known. As a result, the initial activity of the catalyst can be increased, or the activity of the catalyst after regeneration, especially its activity to isomerize ethylbenzene, can be returned to the initial high level. This chlorination treatment can also be effected on the catalyst composition during its preapration to introduce chlorine into the catalyst composition. Sometimes, it can be effected by including a chlorine compound as a component of the starting mixture during the isomerization reaction.

According to the isomerization process described above, the activity to isomerize ethylbenzene to xylenes can be maintained for a longer period of time when the catalyst composition containing the crystalline zeolite and alumina having platinum deposited thereon is used.

The following Examples illustrate the present invention more specifically.

EXAMPLE 1

Fifty grams of 1,6-hexane dibromide was added dropwise to 150 cc of an N,N'-dimethylformamide solution containing 35 g of N-methylpyrrolidine, and the mixture was heated at 70° to 80° C. for several hours. The resulting precipitate was separated by filtration, washed with acetone and dried under reduced pressure to 84 g of 1,6-bis(N-methylpyrrolidinium)hexane dibromide (E). By the same procedure, various ammonium salts were prepared from various dibromides and amine compounds in the yields shown in Table 1.

TABLE 1

| Ammonium compound | n | p = q | Yield (%) |
|---|---|---|---|
| A | 4 | 4 | 79 |
| B | 4 | 5 | 77 |
| C | 5 | 4 | 93 |
| D | 5 | 5 | 83 |
| E | 6 | 4 | 99 |
| F | 6 | 5 | ca. 100 |

The n, p and q are those in the following formula.

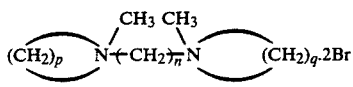

$$(CH_2)_p \underbrace{N(CH_2)_n N}_{CH_3\ CH_3} (CH_2)_q \cdot 2Br$$

EXAMPLE 2

A starting mixture was prepared from 50 g of water glass (containing 36.45% by weight of SiO$_2$ and 17.32% by weight of Na$_2$O), 2.02 g of aluminum sulfate 18-hydrate, 11.3 g of sulfuric acid (97%), 150 g of water and 6.35 g of the organic diammonium compound B synthesized in Example 1.

The mixture had the following composition by mole ratios.

$SiO_2/Al_2O_3 = 100$,

Ammonium salt/Si+Al=0.05, $OH^-/Si+Al = 0.05$, $H_2O/Si+Al = 0.10$, $H_2O/Si+Al = 31$, $OH/H_2O = 3.3 \times 10^{-3}$.

This gel-like starting mixture was charged into a 500 cc stainless steel autoclave and with gentle stirring, reacted at 160° C. under autogenous pressure for 1 week.

The reaction product was taken out, filtered, and fully washed with pure water until the washing had an electric conductivity of not more than 50 micromhos/cm. Drying overnight at 60° C. gave 20.3 g of a zeolite.

The zeolite had the following composition by mole ratios.

$SiO_2/Al_2O_3 = 79.3$, $Na_2O/Al_2O_3 = 0.28$,

RO/Al$_2$O$_3$=1.66 (R represents an organic ammonium group).

The X-ray diffraction data of the resulting zeolite are shown in Table 2, and its X-ray diffraction chart is shown in FIG. 1.

TABLE 2

| d | I/I$_o$ |
|---|---|
| 11.95 sh | Moderate |
| 10.11 | Weak |
| 4.745 sh | Weak |
| 4.260 | Very strong |

TABLE 2-continued

| d | I/I$_o$ |
|---|---|
| 3.883 sh | Strong |
| 3.472 | Moderate |
| 3.401 | Weak |
| 3.351 | Weak |
| 2.525 | Weak |

EXAMPLE 3

A starting mixture was prepared from 60 g of silica sol (Cataloid S30L made by Catalytic Chemical Industry Co., Ltd.; SiO$_2$ 30 wt.%), 2.0 g of aluminum sulfate 18-hydrate, 3.57 g of sodium hydroxide, 100 g of water and 6.35 g of the organic diammonium compound B synthesized in Example 1.

The mixture had the following composition by mole ratios.

$SiO_2/Al_2O_3 = 100$,

Ammonium salt/Si+Al=0.05, $OH^-/Si+Al = 0.20$, $H_2O/Si+Al = 26$, $OH^-/Si+Al = 7.7 \times 10^{-3}$.

This gel-like starting composition was charged into a 500 cc stainless steel autoclave, and reacted at 160° C. under autogenous pressure for 1 week with gentle stirring.

The reaction product was taken out, filtered, and washed with pure water sufficiently until the washing had an electric conductivity of not more than 50 micromhos/cm. Drying overnight at 60° C. gave 18.1 g of a zeolite.

This zeolite had the following composition by mole ratios.

$SiO_2/Al_2O_3 = 88.9$, $Na_2O/Al_2O_3 = 0.50$,

RO/Al$_2$O$_3$=1.95 (R represents an organic ammonium group).

The resulting zeolite was found to be substantially the same as that obtained in Example 2 from its X-ray diffraction data. The X-ray diffraction data are given in Table 3 below.

TABLE 3

| d | I/I$_o$ |
|---|---|
| 11.95 | Moderate |
| 10.11 | Weak |
| 4.733 | Weak |
| 4.250 | Very strong |
| 3.867 sh | Strong |
| 3.466 | Weak |
| 3.345 | Weak |
| 2.522 | Weak |

EXAMPLES 4 TO 24

Zeolites were prepared in the same way as in Examples 2 and 3 using varying materials shown in Table 4. The results are shown in Table 4 including data obtained in Examples 2 and 3.

In all of these Examples, the mole ratio of ammonium to Al+Si was maintained at 0.05; the reaction temperature was 160° C.; and the reaction time was 1 week.

The results of analysis of the resulting zeolites are shown in Table 5 including those obtained in Examples 2 and 3.

TABLE 4

Figure 2:
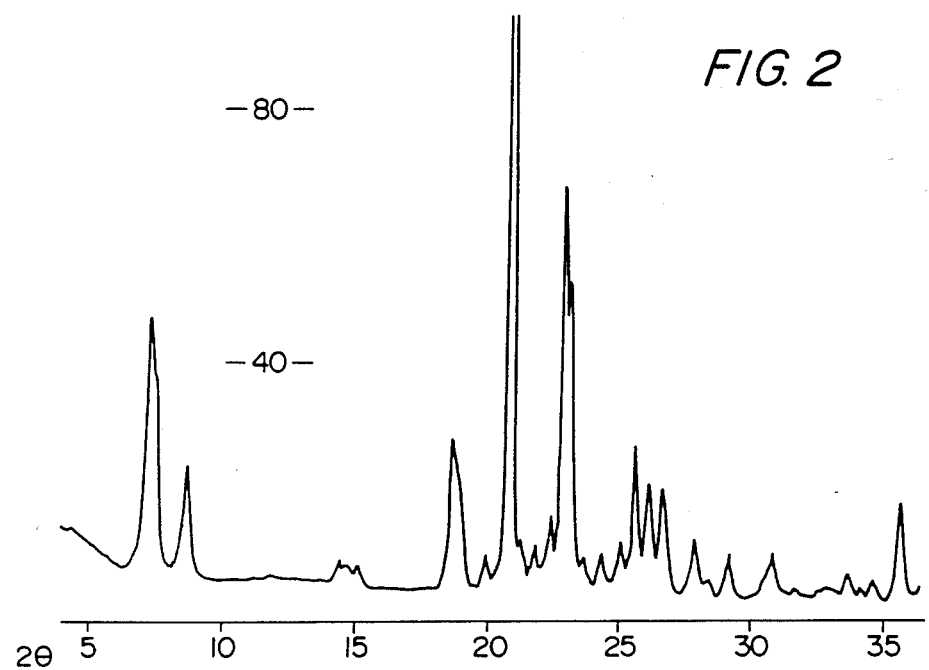

| Example | Organic diammonium compound | Silica source | Feed ratios SiO$_2$/Al$_2$O$_3$ | OH$^-$/Si + Al | H$_2$O/Si + Al | X-ray diffraction data and chart |
|---|---|---|---|---|---|---|
| 4 | A | Water glass | 100 | 0.10 | 31 | Table 2 |
| 5 | A | Silica sol | " | 0.20 | 26 | " |
| 6 | A | Water glass | 200 | 0.10 | 31 | Table 9 |
| 7 | A | Silica sol | infinity | 0.20 | 44 | " |
| 8 | B | Water glass | 20 | 0.21 | 33 | Table 2 + Anal |
| 2 | B | " | 100 | 0.10 | 31 | Table 2 (FIG. 1) |
| 3 | B | Silica sol | " | 0.20 | 26 | Table 3 |
| 9 | B | Water glass | 200 | 0.10 | 31 | Table 8 |
| 10 | B | Silica sol | infinity | 0.20 | 44 | " |
| 11 | C | Water glass | 20 | 0.21 | 33 | Table 2 + Anal |
| 12 | C | " | 100 | 0.10 | 31 | Table 6 |
| 13 | C | Silica sol | " | 0.20 | 26 | Table 7 |
| 14 | C | Water glass | 200 | 0.10 | 31 | Table 9 (FIG. 2) |
| 15 | C | " | infinity | 0.11 | 27 | Table 9 |
| 16 | D | " | 100 | 0.10 | 31 | Table 2 |
| 17 | D | Silica sol | " | 0.20 | 26 | " |
| 18 | D | Water glass | 200 | 0.10 | 31 | Table 9 |
| 19 | D | " | infinity | 0.11 | 27 | Table 9 |
| 20 | E | Water glass | 20 | 0.21 | 33 | Table 2 + Anal |
| 21 | E | " | 100 | 0.10 | 31 | Table 2 |
| 22 | E | Silica sol | " | 0.20 | 26 | " |
| 23 | E | Water glass | 200 | 0.10 | 31 | " |
| 24 | F | Silica sol | " | 0.20 | 26 | " |

(*) Anal in the extreme right column denotes analcite.

TABLE 5

| Example | Composition of product (mole ratio) SiO$_2$/Al$_2$O$_3$ | Na$_2$O/Al$_2$O$_3$ | RO/Al$_2$O$_3$ | X-ray diffraction data and chart |
|---|---|---|---|---|
| 2 | 79.3 | 0.28 | 1.66 | Table 2 (FIG. 1) |
| 3 | 88.9 | 0.50 | 1.95 | Table 3 |
| 9 | 167.1 | 0.46 | 2.37 | Table 8 |
| 12 | 90.9 | 0.34 | 2.03 | Table 6 |
| 13 | 72.1 | 0.39 | 1.56 | Table 7 |
| 14 | 173.5 | 0.60 | 2.73 | Table 9 (FIG. 2) |

(R represents an organic ammonium group.)

TABLE 6

| d | I/I$_o$ |
|---|---|
| 11.95 | Moderate |
| 10.11 | Weak |
| 4.745 sh | Weak |
| 4.260 | Very strong |
| 3.883 sh | Strong |
| 3.460 | Weak |
| 3.401 | Weak |
| 3.339 | Weak |
| 2.522 | Weak |

TABLE 7

| d | I/I$_o$ |
|---|---|
| 11.95 | Moderate |
| 10.11 | Weak |
| 4.733 sh | Weak |
| 4.260 | Very strong |
| 3.883 sh | Very strong |
| 3.460 | Weak |
| 3.395 | Weak |
| 3.339 | Weak |
| 2.522 | Weak |

TABLE 8

| d | I/I$_o$ |
|---|---|
| 11.95 sh | Moderate |
| 10.11 | Weak |
| 4.745 sh | Weak |
| 4.260 | Very strong |
| 3.883 sh | Strong |
| 3.466 | Weak |
| 3.395 | Weak |
| 3.345 | Weak |
| 2.522 | Weak |

TABLE 9

| d | I/I$_o$ |
|---|---|
| 11.95 sh | Moderate |
| 10.11 | Weak |
| 4.745 sh | Weak |
| 4.250 | Very strong |
| 3.883 | Strong |
| 3.842 | Moderate |
| 3.466 | Moderate |
| 3.401 | Weak |
| 3.339 | Weak |
| 2.522 | Weak |

In Tables 2, 3 and 6 to 9 above, "sh" means that the peak has a shoulder. The relative intensities (I/I$_o$) are the same as defined hereinabove.

EXAMPLE 25

Fifteen grams of each of the zeolites obtained in Examples 2 to 6 was calcined at 500° C. for 6 hours, and subjected to ion exchange four times in 100 ml of a 10% aqueous solution of ammonium chloride heated at 70° C. The ion-exchanged zeolites were each dried again and calcined at 500° C. for 6 hours to obtain hydrogen-form zeolites.

Each of the hydrogen-form zeolites was mixed fully with an equal weight of chromatographic alumina gel, and the mixture was pelletized and adjusted to a particle diameter of 10 to 20 mesh.

Five grams of each of the resulting catalysts was activated in an air atmosphere at 450° C. for 8 hours, and filled in a glass reaction tube having an inside diameter of 16 mm and including a thermocouple inserted therein. The reaction tube was heated externally by a nichrome wire heater, and mixed xylenes were passed into the reaction tube in a hydrogen atmosphere at a temperature of 350° C. for 12 hours. The results are shown in Table 10. The mixed xylenes contained 0.5% by weight of toluene, 15% by weight of ethylbenzene, 8% by weight of p-xylene, and 76% by weight of m-xylene and o-xylene combined.

The PX approach to equilibrium (%), Xyl loss (%) and EB disappearance (%), all by weight, in the following tables are defined below.

PX approach to equilibrium (%) =

$$\frac{\begin{pmatrix} PX\text{ concentration} \\ \text{in xylenes in} \\ \text{the product} \end{pmatrix} - \begin{pmatrix} PX\text{ concentration} \\ \text{in xylenes in} \\ \text{the feed} \end{pmatrix}}{\begin{pmatrix} PX\text{ equilibrium} \\ \text{concentration} \\ \text{in xylenes} \end{pmatrix} - \begin{pmatrix} PX\text{ concentration} \\ \text{in xylenes in} \\ \text{the feed} \end{pmatrix}} \times 100$$

$$Xyl\text{ loss }(\%) = \frac{\begin{pmatrix} \text{Xylene con-} \\ \text{centration} \\ \text{of the feed} \end{pmatrix} - \begin{pmatrix} \text{Xylene con-} \\ \text{centration} \\ \text{of the product} \end{pmatrix}}{\text{Xylene concentration of the feed}} \times 100$$

EB disappearance (%) =

$$\frac{\begin{pmatrix} \text{Ethylbenzene} \\ \text{concentration} \\ \text{of the feed} \end{pmatrix} - \begin{pmatrix} \text{Ethylbenzene} \\ \text{concentration} \\ \text{of the product} \end{pmatrix}}{\text{Ethybenzene concentration of the feed}} \times 100$$

TABLE 10

| Catalyst of Example | WHSV (hr$^{-1}$) | H$_2$/HC mole ratio | PX approach to equilibrium (%) | Xyl loss (%) | EB disappearance (%) |
|---|---|---|---|---|---|
| 2 | 4.1 | 1.0 | 101.7 | 13.9 | 26.8 |
| 3 | 4.0 | " | 101.6 | 18.6 | 34.9 |
| 4 | 4.1 | " | 100.7 | 14.8 | 29.9 |
| 5 | " | " | 101.4 | 19.5 | 37.0 |
| 6 | 4.0 | " | 98.8 | 14.0 | 28.3 |

The WHSV was based on the weight of the zeolite contained in the catalyst.

EXAMPLE 26

Twenty-one grams of gamma alumina (ACE-1, a tradename for a product manufactured by Catalytic Chemical Industry Co., Ltd.) was pulverized and suspended in 40 ml of pure water. Then, 21.6 ml of an aqueous solution of chloroplatinic acid containing 11.65 mg of platinum per ml was added. With occasional shaking, the suspension was contacted at 70° C. for 8 hours. The solvent was evaporated by a rotary evaporator under reduced pressure at about 30° C. The residue was dried in an electric desiccator at 100° C. for 6 hours, and calcined in an air atmosphere at 450° C. for 8 hours in an electrical muffle furnace to deposit 1.2% by weight of platinum on alumina.

One part by weight of hydrogen-form zeolite derived in a customary manner from the zeolite obtained in Example 2 was fully mixed with 2 parts by weight of the 1.2 wt.% platinum-deposited alumina obtained as above, and the mixture was pelletized. The particle diameter of the pellets was adjusted to 10 to 20 mesh to obtain a catalyst A.

COMPARATIVE EXAMPLE 1

Catalysts B and C were prepared respectively by the same method as in the preparation of the catalyst A by using hydroen-form mordenite (Zeolon 100H) and H-Y zeolite (obtained by ion-exchanging SK40) as the zeolite component.

EXAMPLE 27

The catalysts obtained in Example 26 and Comparative Example 1 were activated at 450° C. for 8 hours in an electrical muffle furnace in an air atmosphere, and then filled in a reactor with a fixed bed and subjected to a reducing treatment in a stream of hydrogen at 430° to 480° C. under atmospheric pressure for 4 hours. The catalyst bed was then prescribed at each of the temperatures under each of the hydrogen pressures shown in Table 11, and ethylbenzene was passed in the vapor phase through the catalyst bed to isomerize it to xylenes. The results are shown in Table 11.

The converted EB, the produced Xyl and the produced C$_8$N shown in Table 11 are the weights of the converted ethylbenzene, the produced xylenes and the produced C$_8$ naphthene are based on 100 g of ethylbenzene fed.

TABLE 11

| Catalyst | A | A | A | B (comparison) | C (comparison) |
|---|---|---|---|---|---|
| Reaction temperature (°C.) | 360 | 360 | 385 | 370 | 370 |
| WHSV, hr$^{-1}$ | 10.0 | 10.3 | 17.3 | 10.6 | 10.1 |
| Reaction pressure, psia | 80 | 88 | 150 | 104 | 120 |
| H$_2$/HC mole ratio | 7.1 | 3.9 | 2.3 | 7.5 | 7.4 |
| Converted EB | 37.7 | 38.5 | 40.1 | 22.2 | 21.1 |
| Produced Xyl | 20.8 | 21.5 | 21.4 | 8.8 | 4.1 |
| Produced C$_8$N | 8.8 | 9.1 | 9.5 | 12.9 | 14.5 |

Under the conditions shown in Table 12, xylenes containing ethylbenzene were isomerated by using the catalyst A. The results are shown in Table 12.

TABLE 12

| Catalyst | A | |
|---|---|---|
| Reaction temperature (°C.) | 340 | |
| WHSV, hr$^{-1}$ | 3.9 | |
| Reaction pressure, psia | 55 | |
| H$_2$/HC mole ratio | 4.5 | |
| Components | Feed (wt. %) | Product (wt. %) |
| Non-aromatics | 6.5 | 7.6 |
| C$_8$N | 5.7 | 6.1 |
| BZ | 0.8 | 0.7 |
| TOL | 1.5 | 1.7 |
| EB | 10.0 | 8.3 |
| PX | 8.1 | 18.6 |

TABLE 12-continued

| | | |
|---|---|---|
| MX | 50.5 | 42.6 |
| OX | 21.3 | 18.8 |
| C$_9^+$ aromatics | 1.3 | 1.7 |
| PX approach to equilibrium | | 96.0% |
| EB disappearance | | 17.1% |
| Xyl loss | | −0.1% |

EXAMPLE 28

Each of the catalysts obtained in Example 26 and Comnparative Example 1 was activated in an air atmosphere at 450° C. for 8 hours in an electrical muffle furnace, and then filled in a glass reaction tube having a diameter of 16 mm and containing a thermocouple inserted therein and subjected to a reducing treatment in a hydrogen atmosphere at 430° to 480° C. under atmospheric pressure for 4 hours. Then, the catalyst bed was prescribed at the desired temperature, and ethylcyclohexane was passed in the vapor phase through the reaction tube in a stream of hydrogen under atmospheric pressure to perform dehydrogenating isomerization of the naphthene ring. The results are shown in Table 13.

TABLE 13

| Catalyst | | A | B (comparison) | C (comparison) |
|---|---|---|---|---|
| Reaction temperature (°C.) | | 350 | 350 | 350 |
| WHSV, hr$^{-1}$ | | 2.0 | 2.0 | 2.0 |
| H$_2$/HC mole ratio | | 2.4 | 2.0 | 2.0 |
| Non-aromatics | (wt %) | 1.2 | 0.5 | 1.8 |
| C$_8$N | " | 0.1 | 0.2 | 1.6 |
| BZ | " | 4.4 | 1.8 | 0.2 |
| TOL | " | 2.6 | 0.4 | 0.4 |
| EB | " | 58.6 | 85.2 | 91.9 |
| Xyl | " | 21.4 | 4.2 | 0.2 |
| C$_9^+$ aromatics | " | 11.8 | 7.9 | 5.5 |

What we claim is:

1. A process for producing crystalline zeolite TPZ-12, which comprises maintaining a starting mixture at a temperature of at least 80° C. for a period sufficient to produce zeolite crystals, said starting mixture consisting of
   (a) a substance capable of yielding silica under the reaction conditions,
   (b) a water-soluble alkali metal compound,
   (c) water, and
   (d) a diammonium compound represented by the following general formula $$\left[ (CH_2)_p \underset{}{\overset{R_1}{N^\oplus}} (CH_2)_n \underset{}{\overset{R^2}{N^\oplus}} (CH_2)_q \right] \cdot (Y^{m\ominus})_{2/m} \quad (I)$$

wherein R$_1$ and R$_2$ are identical or different and each represents an alkyl group having 1 to 4 carbon atoms, p and q are identical or different and each represents an integer of 4 or 5, n is 4, 5 or 6, and y represents an anion having a valence of m, and optionally,
   (e) a substance capable of yielding alumina under the reaction conditions,
in the quantities represented by the following expressions $$15 \leq [SiO_2]/[Al_2O_3]$$

$$1 \times 10^{-4} \leq [A]/([Si]+[Al]) \leq 1$$

$$1 \times 10^{-4} \leq [OH]/([Si]+[Al]) \leq 0.5$$

$$5 \leq [H_2O]/([Si]+[Al]) \leq 100$$

$$1 \times 10^{-5} \leq [OH]/[H_2O] \leq 1 \times 10^{-1}$$

wherein
[SiO$_2$] represents the amount in moles of the substance capable of yielding silica under the reaction conditions calculated as SiO$_2$,
[Al$_2$O$_3$] represents the amount in moles of the substance capable of yielding alumina under the reaction conditions calculated as Al$_2$O$_3$,
[Si] represents the amount in moles of the substance capable of yielding silica under the reaction conditions calculated as Si,
[Al] represents the amount in moles of the substance capable of yielding alumina under the reaction conditions calculated as Al,
[A] represents the amount in moles of the diammonium compound,
[H$_2$O] represents the amount in moles of water, and
[OH] represents the total amount in moles of the alkali metal compound and the diammonium compound calculated as OH.

2. The process of claim 1 wherein in general formula (I) representing the diammonium compound, n is 4 or 5.

3. The process of claim 1 wherein in general formula (I) representing the diammonium compound, p and q are both 4 and n is 5.

4. The process of claim 1 wherein in general formula (I), p and q are both 5 and n is 4.

5. The process of claim 1 wherein in general formula (I) representing the diammonium compound, R$_1$ and R$_2$ are both methyl groups.

6. The process of claim 1 wherein the starting mixture meets the following quantitative conditions, $$20 \leq [SiO_2]/[Al_2O_3] \leq 2,000$$

$$5 \times 10^{-4} \leq [A]/([Si]+[Al]) \leq 0.5$$

$$1 \times 10^{-3} \leq [OH]/([Si]+[Al]) \leq 0.4$$

$$10 \leq [H_2O]/([Si]+[Al]) \leq 50$$

$$1 \times 10^{-4} \leq [OH]/[H_2O] \leq 1 \times 10^{-1}.$$

7. The process of claim 1 wherein the starting mixture meets the following quantitative conditions, $$20 \leq [SiO_2]/[Al_2O_3] \leq 250$$

$$1 \times 10^{-3} \leq [A]/([Si]+[Al]) \leq 1 \times 10^{-1}$$

$$5 \times 10^{-3} \leq [OH]/([Si]+[Al]) \leq 0.3$$

$$15 \leq [H_2O]/([Si]+[Al]) \leq 50$$

$$1 \times 10^{-4} \leq [OH]/[H_2O] \leq 1 \times 10^{-2}.$$

8. The process of claim 1 wherein the temperature is 100° to 200° C.

9. The process of claim 3 wherein R$_1$ and R$_2$ are both methyl groups.

10. The process of claim 4 wherein $R_1$ and $R_2$ are both methyl groups.

11. The process of claim 1 wherein the crystalline zeolite has the composition of the following formula (IV) in the form of an oxide in an anhydrous condition:

$$xM_{2/t}O.yAl_2O_3.SiO_2 \qquad (IV)$$

wherein M represents at least one type of cation having a valence of t, x represents a number from 0 to 0.4, and y is a number from 0 to 0.1.

12. The process of claim 11 wherein the crystalline zeolite is further characterized by at least the following significant peaks:

| Interplanar spacing d (Å) | Relative intensity (I/I$_0$) |
|---|---|
| 11.9 ± 0.5 | Moderate |
| 10.1 ± 0.5 | Weak |
| 4.74 ± 0.1 | Weak |
| 4.25 ± 0.1 | Very strong |
| 3.88 ± 0.05 | Strong |
| 3.47 ± 0.04 | Moderate to weak |
| 3.40 ± 0.04 | Weak |
| 3.34 ± 0.04 | Weak |
| 2.53 ± 0.03 | Weak | wherein the peak at 3.88±0.05 may have a shoulder or be split.

13. The process of claim 12 wherein in formula (IV) x is a number of from 0.025 to 0.08 and y is a number of from 0.005 to 0.02.

* * * * *